United States Patent
Kavusi et al.

(10) Patent No.: US 9,075,041 B2
(45) Date of Patent: Jul. 7, 2015

(54) METHODS FOR GENERATING PH/IONIC CONCENTRATION GRADIENT NEAR ELECTRODE SURFACES FOR MODULATING BIOMOLECULAR INTERACTIONS

(75) Inventors: Sam Kavusi, Menlo Park, CA (US); Rajan Gangadharan, Mountain House, CA (US); Christopher Johnson, Mountain View, CA (US); Aldrich N. K. Lau, Palo Alto, CA (US); Piyush Verma, Sunnyvale, CA (US)

(73) Assignee: ROBERT BOSCH GMBH, Stuttgart (DE)

( * ) Notice: Subject to any disclaimer, the term of this patent is extended or adjusted under 35 U.S.C. 154(b) by 420 days.

(21) Appl. No.: 13/543,300

(22) Filed: Jul. 6, 2012

(65) Prior Publication Data

US 2014/0008244 A1   Jan. 9, 2014

(51) Int. Cl.
*G01N 33/50* (2006.01)
*G01N 27/327* (2006.01)
*G01N 33/53* (2006.01)

(52) U.S. Cl.
CPC ............ *G01N 33/50* (2013.01); *G01N 27/3275* (2013.01); *G01N 33/5306* (2013.01)

(58) Field of Classification Search
CPC .................................................. G01N 27/3275
USPC ............. 204/412, 403.01–403.15; 205/777.5, 205/778, 792; 422/50
See application file for complete search history.

(56) References Cited

U.S. PATENT DOCUMENTS

| | | | |
|---|---|---|---|
| 6,618,934 B1 | 9/2003 | Feldman et al. | |
| 6,797,152 B2 | 9/2004 | Freund et al. | |
| 6,887,714 B2 | 5/2005 | Fritsch et al. | |
| 7,785,785 B2 | 8/2010 | Pourmand et al. | |
| 8,906,617 B2 | 12/2014 | Rothberg et al. | |
| 8,932,868 B2 | 1/2015 | Van Grinsven et al. | |
| 2009/0026082 A1 | 1/2009 | Rothberg et al. | |
| 2009/0061524 A1* | 3/2009 | Rishpon et al. | 436/86 |
| 2010/0285601 A1* | 11/2010 | Kong et al. | 436/94 |
| 2011/0091870 A1 | 4/2011 | Lang et al. | |
| 2012/0085660 A1 | 4/2012 | Rothberg et al. | |
| 2012/0164351 A1* | 6/2012 | Gindilis | 427/561 |

FOREIGN PATENT DOCUMENTS

| | | |
|---|---|---|
| WO | WO 2011/047020 | 4/2011 |
| WO | WO 2012/076350 | 6/2012 |
| WO | WO 2012/116385 | 9/2012 |

OTHER PUBLICATIONS

Page 234 of Ribéreau-Gayon et al. Handbook of Enology, vol. 1—The Microbiology of Wine and Vinifications, 2nd ed. John Wiley & Sons, Ltd 2006.*

(Continued)

*Primary Examiner* — Alex Noguerola
(74) *Attorney, Agent, or Firm* — Kenyon & Kenyon LLP

(57) ABSTRACT

Methods of modulating the binding interactions between a (biomolecular) probe or detection agent and an analyte of interest from a biological sample in a biosensor having a multisite array of test sites. In particular, the methods modulate the pH or ionic concentration gradient near the electrodes in such biosensor. The methods of modulating the binding interactions provide a biosensor and analytic methods for more accurately measuring an analyte of interest in a biological sample.

35 Claims, 5 Drawing Sheets

(56) References Cited

OTHER PUBLICATIONS

"Simazine" entry obtained from the EXTOXNET (Extension Toxicology Network) website http://pmep.cce.cornell.edu/profiles/extoxnet/pyrethrins-ziram/simazine-ext.html, published Sep. 1993, downloaded Nov. 7, 2014.*

International Search Report dated Sep. 17, 2013 of the corresponding International Application PCT/US2013/047563 filed Jun. 25, 2013.

Zeravik et al., "A highly sensitive flow-through amperometric immunosensor based on the Peroxidase chip and enzyme-channeling principle", Biosensors and Bioelectronics, vol. 18 No. 11, Oct. 1, 2003, pp. 1321-1327.

Kozlovskaja et al., "Response of hydrogen peroxide, ascorbic acid, and paracetamol at a platinum electrode coated with microfilms of polyaniline", Microchimica Acta; An International Journal on Micro and Traceanalysis, Springer-Verlag, VI, vol. 166, No. 3-4, Jul. 28, 2009, pp. 229-234.

Chang et al., "Glucose concentration determination based on silica sol-gel encapsulated glucose oxidase optical biosensor arrays", Talanta, Elsevier, Amsterdam, NL, vol. 83, No. 1, Nov. 15, 2010, pp. 61-65.

Hotta et al., "In situ monitoring of the H<+> concentration change near an electrode surface through electrolysis using slab optical waveguide pH sensor", Electrochemistry Communications, Elsevier, Amsterdam, NL, vol. 10, No. 9, Sep. 1, 2008, pp. 1351-1354.

Liu et al., "pH-switchable bioelectroatalysis based on layer-by-layer films assembled with glucose oxidase and branched poly(ethyleneimine)", Sensors and Actuators B: Chemical: International Journal Devoted to Research and Development of Physical and Chemical Transducers, Elsevier S.A., Switzerland, vol. 156, No. 2, Feb. 7, 2011, pp. 645-650.

Mu et al., "Catechol sensor using poly(aniline-co-o-arninophenol) as an electron transfer mediator", Biosensors and Bioelectronics, Elsevier BV, NL, vol. 21, No. 7, Jan. 15, 2006, pp. 1237-1243.

Gao et al., "A DNA biosensor based on a morpholino oligomer coated indium-tin oxide electrode and a cationic redox polymer", The Analyst, vol. 134, No. 5, Jan. 1, 2009, p. 952.

\* cited by examiner

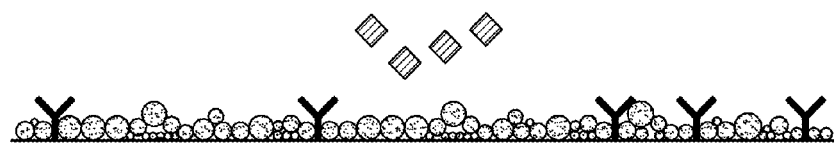
FIG. 1(A)
FIG. 1(B)
FIG. 1(C)
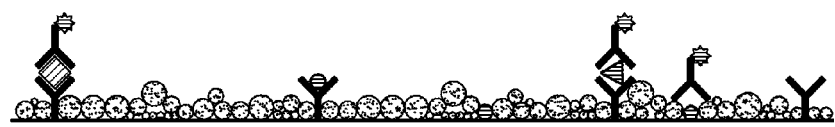
FIG. 2

METHODS FOR GENERATING PH/IONIC CONCENTRATION GRADIENT NEAR ELECTRODE SURFACES FOR MODULATING BIOMOLECULAR INTERACTIONS

FIELD OF THE INVENTION

The invention relates to a diagnostic method for biomolecules using a biosensor and methods of improving such biosensor. Moreover, the invention relates to a method for generating a pH concentration gradient near electrode surfaces for modulating biomolecular interactions in such biosensor.

BACKGROUND INFORMATION

Recently there has been an increased interest in predictive, preventative, and particularly personalized medicine which requires diagnostic tests with higher fidelity, e.g., sensitivity and specificity. Multiplexed measurement platforms, e.g., protein arrays currently used in research, are among the promising diagnostics technologies for the near future. The samples in these tests can be human body fluids such as blood, serum, saliva, biological cells, urine, or other biomolecules but can also be consumables such as milk, baby food, or water. Within this field there is a growing need for low-cost, multiplexed tests for biomolecules such as nucleic acids, proteins, and also small molecules. Achieving the sensitivity and specificity needed in such tests is not without difficult challenges. Combining these tests with integrated electronics and using CMOS technology has provided solutions to some of the challenges.

The two main limitations in a detection assay include sensitivity and cross-reactivity. Both of these factors affect the minimum detectable concentration and therefore the diagnostic error rate. The sensitivity in such tests is generally limited by label detection accuracy, association factor of the probe-analyte pair (for example an antibody-antigen pair), and the effective density of probe molecule (for example probe antibody) on the surface (as shown in FIG. 1). Other molecules in the biological sample can also affect the minimum detectable concentration by binding to the probe molecule (for example the primary antibody), or by physisorption of the analyte to the surface at the test site (as shown in FIG. 2). The detection agent (for example a secondary antibody) may also physisorb to the surface causing an increase in the background signal (as shown in FIG. 2). Solving the cross-reactivity and background problem can take a significant amount of time in the assay development of a new test and increases the cost and complexity of the overall test. The assay is typically optimized by finding the best reagents and conditions and also by manufacturing the most specific probe molecule (for example antibody). This results in a long development time, the infeasibility of tests in some cases, and a higher manufacturing cost. For example a typical development of an ELISA assay requires several scientists working for more than a year finding the correct antibody as part of the assay development. Cross-reactivity of the proteins may be the source of the failure of such an effort.

A biosensor providing a multiple site testing platform was thought to provide a solution to some of the above described limitations in assay development. US Published Patent Application US 2011/0091870 describes such biosensor having multiple sites that could be subjected to different reaction conditions to modulate the binding of the biomolecular analyte (for example proteins) to the probe molecule. For example the signal detected in a biosensor having four sites also can have several components, e.g. four. These four terms may correspond to the concentration of the biomarker of interest, concentration of interfering analytes in the sample that bind non-specifically to primary antibody (probe molecule) sites and prevent the biomarker to bind, concentration of interfering analytes in the sample that form a sandwich and produce wrong signal, and finally the concentration of interfering analytes in the sample that physisorb to the surface and produce wrong signal. Each term is also proportional to a binding efficiency factor, $\alpha_{ij}$, which is a function of the molecule affinities and other assay conditions, e.g., mass transport. By controlling the condition at each site separately, different sites will have different efficiency factors. Accurate measurement of the signal at each site will result in multiple equations and multiple unknowns for example, $$\begin{cases} S_1 = \alpha_{11}C_{an} - \alpha_{12}C_{j1} + \alpha_{13}C_{j2} + \alpha_{14}C_{j3} \\ S_2 = \alpha_{21}C_{an} - \alpha_{22}C_{j1} + \alpha_{23}C_{j2} + \alpha_{24}C_{j3} \\ S_3 = \alpha_{31}C_{an} - \alpha_{32}C_{j1} + \alpha_{33}C_{j2} + \alpha_{34}C_{j3} \\ S_4 = \alpha_{41}C_{an} - \alpha_{42}C_{j1} + \alpha_{43}C_{j2} + \alpha_{44}C_{j3} \end{cases} \Longrightarrow C_{an}$$

where $C_{an}$ corresponds to the targeted biomolecular analyte concentration and $C_{j1}$, $C_{j2}$, $C_{j3}$ correspond to the total concentration of molecules which result in different terms in background signal.

Accurate and precise control of the assay conditions at different sites to generate large changes in the binding efficiency factors is important in the performance of such biosensor as a detection system for a biomolecular analyte of interest. Thus, there is a need for methods that can be readily integrated with a CMOS, electrode array, or TFT based setup to generate large change in binding efficiencies between test sites in a biosensor having an array of multiple test sites.

SUMMARY OF THE INVENTION

Herein are provided such methods that can be integrated with for example a CMOS, electrode array, or TFT based biosensor to generate large changes in binding efficiencies between test sites in the biosensor having an array of multiple test sites. In particular, the current application provides methods to modulate the pH or ionic concentration near electrode surfaces of such biosensors in order to modulate the biomolecular interactions between a probe biomolecule and a biomolecular analyte of interest.

In one embodiment there is provided a method of modulating the pH or ionic concentration in a biosensor, the method comprising:

a) providing a biosensor comprising a multisite array of test sites in which the conditions for interacting with a biomolecule analyte can be varied independently, each test site comprising a support in an aqueous solution, the support comprising one or more electrodes or an electromagnet, and a biomolecule interface layer having one or more immobilized probes thereon;

b) adding an electrochemically active agent, an enzyme, an enzyme substrate, a buffer inhibitor, or a combination thereof to the aqueous solution; and c) reacting the electrochemically active agent, the enzyme, the enzyme substrate, or a combination thereof in the aqueous solution to produce $H^+$ ion or $OH^-$ ions, or increasing the diffusion of $H^+$ ions or $OH^-$ ions with the buffer inhibitor, or inhibiting the interaction between $H^+$ ions or $OH^-$ ions and buffering salts with the buffer inhibitor.

In another embodiment there is provided a method of modulating the pH or ionic concentration in a biosensor, the method comprising:
a) providing a biosensor comprising a multisite array of test sites in which the conditions for interacting with a biomolecule analyte can be varied independently, each test site comprising a support in an aqueous solution, the support comprising one or more electrodes or an electromagnet, and a biomolecule interface layer having one or more immobilized probes;
b) adding an electrochemically active agent to the aqueous solution; and
c) oxidizing or reducing the electrochemically active agent.

In another embodiment there is provided a method of modulating the pH or ionic concentration in a biosensor, the method comprising:
a) providing a biosensor comprising a multisite array of test sites in which the conditions for interacting with a biomolecule analyte can be varied independently, each test site comprising a support in an aqueous solution, the support comprising one or more electrodes or an electromagnet, and a biomolecule interface layer having one or more immobilized probes and one or more immobilized enzymes thereon;
b) adding an enzyme substrate to the aqueous solution; and
c) enzymatically oxidizing or reducing the enzyme substrate.

In yet another embodiment there is provided a method of modulating the pH or ionic concentration in a biosensor, the method comprising:
a) providing a biosensor comprising a multisite array of test sites in which the conditions for interacting with a biomolecule analyte can be varied independently, each test site comprising an electromagnet in an aqueous solution and a biomolecule interface layer having one or more immobilized probes;
b) adding one or more enzymes immobilized onto magnetic micro- or nano-particles to the aqueous solution;
c) adding an enzyme substrate to the aqueous solution; and
d) enzymatically oxidizing or reducing the enzyme substrate.

In another embodiment there is provided a method of modulating the pH or ionic concentration in a biosensor, the method comprising:
a) providing a biosensor comprising a multisite array of test sites in which the conditions for interacting with a biomolecule analyte can be varied independently, each test site comprising a support in an aqueous solution, the support comprising one or more electrodes or an electromagnet, and a biomolecule interface layer having one or more immobilized probes;
b) adding an enzyme to the aqueous solution; and
c) reacting the enzyme at the electrode surface.

In another embodiment there is provided a method of modulating the pH or ionic concentration in a biosensor, the method comprising:
a) providing a biosensor comprising a multisite array of test sites in which the conditions for interacting with a biomolecule analyte can be varied independently, each test site comprising a support in an aqueous solution, the support comprising one or more electrodes or an electromagnet, and a biomolecule interface layer having one or more immobilized probes;
b) adding a buffer inhibitor to the aqueous solution; and
c) inhibiting the diffusion of $H^+$ ions or $OH^-$ ions or the interaction between $H^+$ ions or $OH^-$ ions and buffering salts.

In yet another embodiment there is provided a biosensor for use in detecting a biomolecule analyte comprising a multisite array of test sites in which the conditions for interacting with the biomolecule analyte can be varied independently, each test site comprising:
a) a support in an aqueous environment;
b) one or more electrodes; and
c) a biomolecule interface layer having one or more immobilized probes and one or more immobilized enzymes.

In another embodiment there is provided a method for detecting a biomolecule analyte in a biological sample, the method comprises:
a) providing a biosensor comprising a multisite array of test sites in which the conditions for interacting with a biomolecule analyte can be varied independently, each test site comprising a support in an aqueous solution comprising a water-miscible organic co-solvent, e.g., acetonitrile, dimethyl sulfoxide (DMSO), dimethyl formamide (DMF), and N,N-dimethyl acetamide (DMAc), to facilitate the dissolution of an electrochemical active agent, the support comprising one or more electrodes or an electromagnet, and a biomolecule interface layer having one or more immobilized probes thereon;
b) adding in each test site an electrochemically active agent, an enzyme, an enzyme substrate, a buffer inhibitor, or a combination thereof to the aqueous solution;
c) reacting the electrochemically active agent, the enzyme, the enzyme substrate, or a combination thereof in the aqueous solution to produce $H^+$ ion or $OH^-$ ions, or increasing the diffusion of $H^+$ ions or $OH^-$ ions with the buffer inhibitor, or the inhibiting the interaction between $H^+$ ions or $OH^-$ ions and buffering salts with the buffer inhibitor;
d) adding a biological sample to each test site; and
e) detecting the biomolecule analyte in each test site,
wherein the amounts added in step b) and the reaction in step c) are varied between test sites in a subset array of test sites in order to obtain sets of test sites in which the pH or ionic concentration near the electrode surfaces in the test sites varies.

BRIEF DESCRIPTION OF THE FIGURES

FIG. 1: Illustration of the steps of a typical and well known ELISA assay: a) Sample introduced to immobilized primary antibody on a blocked surface and incubated, b) Sample washed, and c) labeled secondary antibody is added. The number of labels is proportional to the concentration of target antigen.

FIG. 2: Illustration of the undesired cross-reactivity. Molecules other than the antigen of interest (diamond) can bind to primary antibody or the surface and either create incorrect signal or prevent the antigen in forming a sandwich.

DETAILED DESCRIPTION

Figure 3:
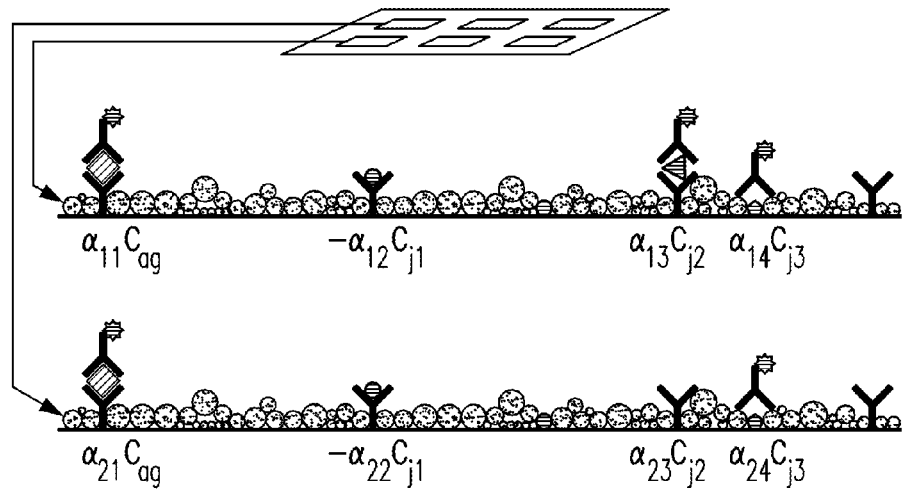
FIG. 3: Illustration of the multisite sensor and the components in the detected signal. The two schematics on the bottom correspond to two of the sites.

In order to vary the pH or ionic concentration gradient in a multisite array of test sites in a biosensor there is provided a method of modulating the pH or ionic concentration in a biosensor, the method comprising:

a) providing a biosensor comprising a multisite array of test sites in which the conditions for interacting with a biomolecule analyte can be varied independently, each test site comprising a support in an aqueous solution, the support comprising one or more electrodes or an electromagnet, and a biomolecule interface layer having one or more immobilized probes thereon;

b) adding an electrochemically active agent, an enzyme, an enzyme substrate, a buffer inhibitor, or a combination thereof to the aqueous solution; and c) reacting the electrochemically active agent, the enzyme, the enzyme substrate, or a combination thereof in the aqueous solution to produce H$^+$ ion or OH$^-$ ions, or increasing the diffusion of H+ ions or OH– ions with the buffering agent or inhibiting the interaction between H$^+$ ions or OH$^-$ ions and buffering salts with the buffer inhibitor.

In the above described method a local pH or ionic concentration gradient can be obtained in the various test sites in a multisite array biosensor. The variation of the local pH and/or ionic concentration gradient at the electrode, and in particular in the vicinity of the (biomolecular) probe in a biomolecular interface layer, over subsets of the multisite array of the biosensor, allows for modulating the binding efficiency of the (biomolecular) probe and an analyte to be tested from a biological sample. The analyte of interest, when bound to the (biomolecular) probe, can be then detected using a detection agent, such as for example a labeled secondary antibody. The modulation of binding efficiencies in a subset of a multisite array provides a method for the accurate determination of such analyte of interest.

The biosensor preferably comprises a multisite array of test sites as for example is described in US 2011/0091870. Such multisite array preferably includes a number of different subarrays/subsets of test sites. Each test sites represents a site for performing an analysis of a (biomolecular) analyte from a biological sample through the detection of the (biomolecular) analyte using a (biomolecular) probe. The analytical conditions in each test site in each of the subarrays/subsets may be varied to obtain a collection of varied signals that will result in multiple equations and multiple unknowns from which the concentration of the (biomolecular) analyte can be determined in order to obtain an accurate measurement of the (biomolecular) analyte.

The multiple unknowns in the obtained varied signals each includes a term that is proportional to a binding efficiency factor, $\alpha_{ij}$, and the concentrations of the various molecules in the biological sample binding that are detected at the test site. The multiple equations with multiple unknowns may be represented for example as follows, $$\begin{cases} S_1 = \alpha_{11}C_{an} - \alpha_{12}C_{j1} + \alpha_{13}C_{j2} + \alpha_{14}C_{j3} \\ S_2 = \alpha_{21}C_{an} - \alpha_{22}C_{j1} + \alpha_{23}C_{j2} + \alpha_{24}C_{j3} \\ S_3 = \alpha_{31}C_{an} - \alpha_{32}C_{j1} + \alpha_{33}C_{j2} + \alpha_{34}C_{j3} \\ S_4 = \alpha_{41}C_{an} - \alpha_{42}C_{j1} + \alpha_{43}C_{j2} + \alpha_{44}C_{j3} \end{cases} \Longrightarrow C_{an}$$

where $C_{an}$ corresponds to the targeted biomolecular analyte concentration and $C_{j1}$, $C_{j2}$, $C_{j3}$ correspond to the total concentration of molecules which result in different terms in background signal, from which collection of multiple equations the concentration of the targeted biomolecular analyte can be determined.

The number of subarrays/subsets, as well as the number of test sites within each subarray/subset may be varied, as needed to obtain such accurate measurement of the analyte. Some of these analytical conditions include parameters such as for example temperature, shear stress, and pressure. For example the temperature of the aqueous solution in which the biomolecular probe and analyte of interest in the biological sample interact can be varied using the electromagnetic heat at the test site. Another important condition for the interaction between the biomolecular probe and the analyte of interest is the pH or ionic concentration. The method described herein modulates this pH or ionic concentration in the local environment of the biomolecular probe in order to affect the binding efficiency in the vicinity of the biomolecular probe.

Figure 4:
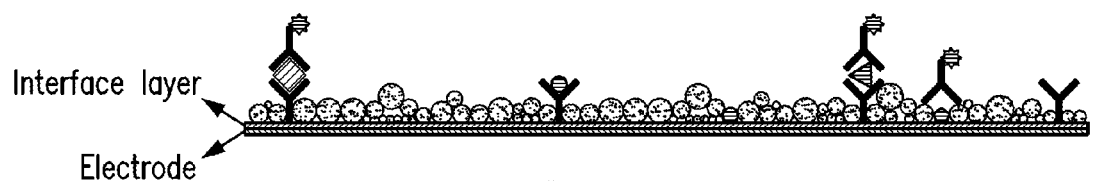
FIG. 4: Illustration of the composition of a sensor test site in a multisite sensor.

Each test site in the subarray/subset of the multiple site array comprises a support onto which one or more electrodes are placed and onto which solid surface the biomolecular probe(s) are immobilized or bound (as shown in FIGS. 3 and 4). This immobilization of biomolecular probes to a solid surface or support assists in reducing the amount of probe needed for the analytical method and also localizes the detection area to make accurate measurements. The biomolecular probes are therefore attached to solid surfaces of the support and/or electrodes such as those of silicon, glass, metal and semiconductor materials (as shown in FIG. 4).

Figure 5:
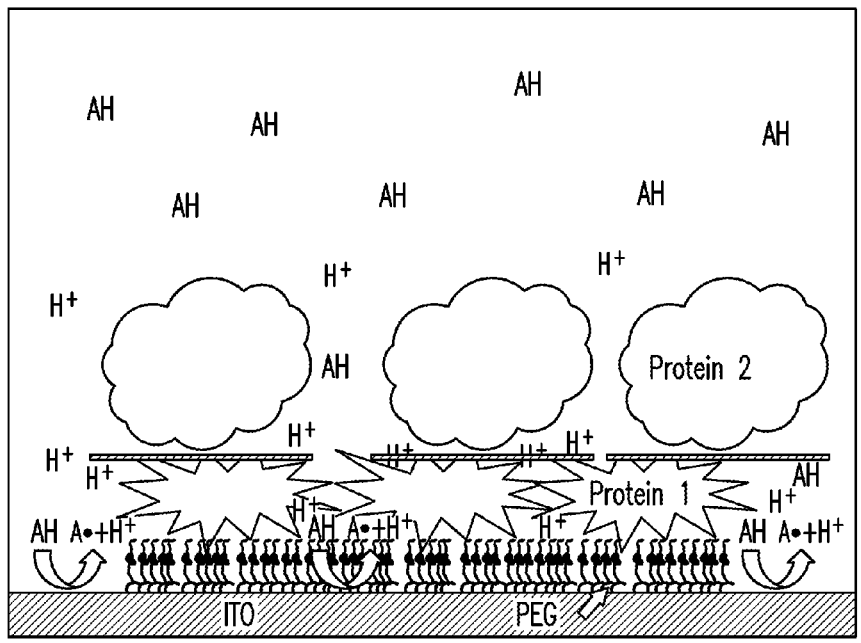
FIG. 5: Schematic of the pH change on an electrode surface using electrochemical method.

The biomolecular probe is attached or immobilized onto the support and/or electrode(s) within a biomolecular interface layer (as shown in FIG. 4). The biomolecular layer includes a layer of immobilized polymers, preferably a silane immobilized polyethylene glycol (PEG). Surface-immobilized polyethylene glycol (PEG) can be used to prevent non-specific adsorption of biomolecular analytes onto surfaces. At least a portion of the surface-immobilized PEG can comprise terminal functional groups such as N-hydroxysuccinimide (NHS) ester, maleimide, alkynes, azides, streptavidin or biotin that are capable of conjugating. The biomolecular probe may be immobilized by conjugating with the surface-immobilized PEG. It is important that the method used to change the pH does not impair the covalent binding of for example the PEG onto the surface of a solid support, or the linker that conjugated the biomolecular probe to the PEG (as shown in FIG. 5). The method of modulating the pH or ionic concentration as described herein can protect these surface chemistries, while affecting a pH/ionic concentration change in the environment of the biomolecular probe.

A suitable biomolecular probe can be a carbohydrate, a protein, a glycoprotein, a glycoconjugate, a nucleic acid, a cell, or a ligand for which the analyte of interest has a specific affinity. Such probe can for example be an antibody, an antibody fragment, a peptide, an oligonucleotide, a DNA oligonucleotide, a RNA oligonucleotide, a lipid, a lectin that binds with glycoproteins and glycolipids on the surface of a cell, a sugar, an agonist, or antagonist. In a specific example, the biomolecular probe is a protein antibody which interacts with an antigen that is present for example in a biological sample, the antigen being a biomolecular analyte of interest.

In the analytical method described herein the analyte of interest in a biological sample can be for example a protein, such as an antigen or enzyme or peptide, a whole cell, components of a cell membrane, a nucleic acid, such as DNA or RNA, or a DNA oligonucleotide, or a RNA oligonucleotide.

The electrodes can be any electrode suitable in a biosensor for example indium tin oxide (ITO), gold, or silver electrodes. In a preferred embodiment the electrodes in the biosensor in the method described herein are indium tin oxide (ITO) electrodes.

This analytical method using a biosensor for detecting a biomolecule analyte in a biological sample according to one embodiment is a method which comprises the steps of:

a) providing a biosensor comprising a multisite array of test sites in which the conditions for interacting with a biomolecule analyte can be varied independently, each test site comprising a support in an aqueous solution, the support comprising one or more electrodes or an electromagnet, and a biomolecule interface layer having one or more immobilized detection agents thereon;

b) adding in each test site an electrochemically active agent, an enzyme, an enzyme substrate, a buffer inhibitor, or a combination thereof to the aqueous solution;

c) reacting the electrochemically active agent, the enzyme, the enzyme substrate, or combination thereof in the aqueous solution to produce $H^+$ ion or $OH^-$ ions, or increasing the diffusion of $H^+$ ions or $OH^-$ ions with the buffer inhibitor, or inhibiting the interaction between $H^+$ ions or $OH^-$ ions and buffering salts with the buffer inhibitor;

d) adding a biological sample to each test site; and e) detecting the biomolecule analyte in each test site, wherein the amounts added in step b) and the reaction in step c) are varied between test sites in a subset array of test sites in order to obtain sets of test sites in which the pH or ionic concentration near the electrode surfaces in the test sites varies. The aqueous solution comprises a water-miscible organic co-solvent, e.g., acetonitrile, dimethyl sulfoxide (DMSO), dimethyl formamide (DMF), and N,N-dimethyl acetamide (DMAc), to facilitate the dissolution of an electrochemical active agent. The amount of water-miscible organic solvent can range from 0.1 to 80% v/v, preferably from 0.1 to 10% v/v, most preferably from 1.0 to 5.0% v/v in respect to water in the aqueous solution. The analytical method hereby obtains in each subset of test sites a pH or ionic concentration gradient over the test sites in the subset in the vicinity of the biomolecular probe. The binding efficiencies of the analyte and any other molecule in the biological sample is thereby differently affected in each series of test sites in each subset.

Figure 6:
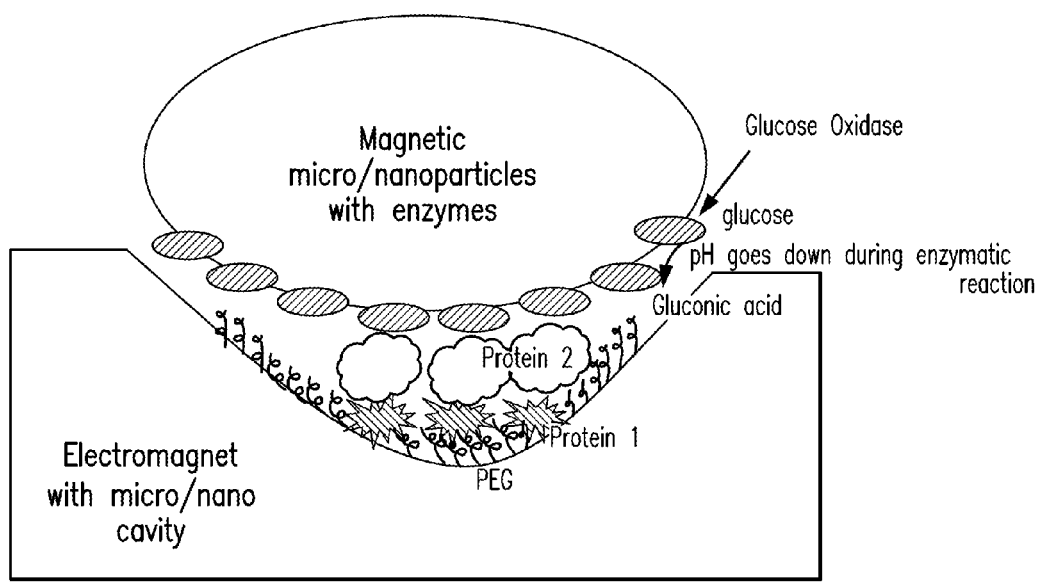
FIG. 6: Illustration of pH change by enzymatic reactions when they are brought close to the protein surface using magnetic micro/nanoparticles. The micro/nano cavity helps in localizing the pH change.

The biomolecular analyte can be detected using any suitable detection method. Known detection methods of such analyte include luminescence, fluorescence, colorimetric methods, electrochemical methods, impedance measurements, or magnetic induction measurements. In various of such methods the analyte binds to the immobilized biomolecular probe and a detection agent such as for example a secondary labeled probe that specifically binds to the analyte, bound to the immobilized probe, is introduced. This detection agent or secondary labeled probe gives rise to a detectable signal such as for example luminescence or fluorescence (as shown in FIGS. 5 and 6).

In such analytical method the pH of the solution surrounding the immobilize biomolecular probe has been known to influence the binding/activity between the probe and the analyte to a great extent. Concentration of other ions on surrounding proteins can also heavily influence the binding/activity. Herein are provided methods to modulate the pH and/or ionic concentration in the vicinity of the biomolecular probe immobilized close to a surface. The modulation of the pH near these solid surfaces also affect the non-specific interactions of the analyte to other molecules than the biomolecular probe and the interactions of other molecules in the solution of the biological sample with the biomolecular probe or analyte. The modulation of pH or ionic concentration however should not impair any of the surface chemistries, such as those that immobilize the biomolecular probe to its solid support in a test site of a multisite array in the biosensor. The method of modulating the pH or ionic concentration as described herein can protect these surface chemistries, while affecting a pH/ionic concentration change in the environment of the biomolecular probe.

Surface chemistry compatibility is an important consideration that should be noted when the methods described herein are practiced. pH change is caused by changes in hydrogen ion or hydroxyl ion concentrations. A variety of chemical reactions taken place at electrode-liquid, electrode-cross linker, cross linker-protein, and protein-protein interfaces as shown in FIG. 5 can also become a hindrance to pH changes happening near the solid surfaces to reach the proteins on top of them. They can simply act as diffusion barriers for the ions and hinder the pH changes around the biomolecular probes and analytes. These methods of modulating the pH or ionic concentration described herein helps in maximizing the changes in hydrogen or hydroxyl ion concentration so that they can overcome any diffusion barrier imposed by the surface chemistry.

Another important aspect is the buffering capacity of the solution in contact with the solid interface. The buffering effect can be large enough that the pH change at the interface would never reach the biomolecular probes that are immobilized away from it. The distance can vary based on the biomolecular interface layer deposited on top of the solid interface. Such biomolecular interface layer may have a thickness of 300 nm or less, preferable between 1-150 nm, even more preferably between 5-100 nm. As such the distance between the solid interface and the biomolecular probe within the biomolecular interface layer can range between 0.1-300 nm. Use of buffer inhibitors in the solution or on the surface that extend the pH change on the electrode interface to reach the interacting probe-analyte pair may contribute to modulating the pH or ionic concentration in the vicinity of the biomolecular probe.

Following are examples of methods for modulating the pH/ionic concentration at the solid-liquid interfaces. These include: 1) the electrochemical generation of ions at electrode surfaces by adding an electrochemically active species to the solution which generates ions of interest (e.g., H+, Mg+, OH−) upon electrochemical oxidation/reduction; 2) bringing enzymes close to the site of interest, which release such ions of interest from an enzyme substrate that is reacted with the enzyme; 3) the introduction of buffer inhibitors, for example, by mixing polymers that selectively reduce the diffusion rate of ions in the solution (e.g., phosphate). U.S. Pat. No. 7,948, 015 describes the use of such inhibitors for applications in which measuring small local pH changes is of interest (e.g., in DNA sequencing). However in the methods of locally modulating the pH similar inhibitors can be used in order to extend the local pH changes further away from the electrode-liquid interface; and 4) the redistribution of preexisting ions near the electrode surface due to electrostatic forces.

In one embodiment of a method for modulating the pH or ionic concentration in a biosensor as described herein an electrochemically active agent is added to the aqueous solution at a test site in a multisite array, wherein the test site has a biomolecular interface layer comprising a biomolecular probe or detection agent and oxidizing or reducing the electrochemically active agent. The electrochemically active agent may be added at a concentration of 1 nM to 100 mM, preferably at a concentration between 10 nM and 10 mM, more preferably at a concentration of 100 nM and 5 mM. The electrochemically active agent may be electro-oxidized or electro-reduced at an electrode potential in the range of −2V to +2V (vs. Ag/AgCl reference electrode). Preferably the electrode potential is in the range of −1V to +1V, even more preferably the electrode potential is in the range of −0.5V to +0.5V.

Suitable electrochemically active agents include dopamine hydrochloride, ascorbic acid, phenol and derivatives, benzoquinones and derivatives, for example, 2,5-dihydroxy-1,4-benzoquinone, 2,3,5,6-tetrahydroxy-1,4-benzoquinone and 2,6-dichloroquinone-4-chloroimide; naphthoquinones and derivatives, for example, hydroxy-1,4-naphthoquinone, 5,8-dihydroxy-1,4-naphthoquinone, and potassium 1,4-naphthoquinone-2-sulfonate; and 9,10-anthraquinone and derivatives, for example, sodium anthraquinone-2-carboxylate, potassium 9,10-anthraquinone-2,6-disulfonate.

In another embodiment of a method for modulating the pH or ionic concentration in a biosensor, an enzyme is immobilized in a biomolecule interface layer also having one or more immobilized biomolecular probers. An enzyme substrate is then added to the aqueous solution at a test site in a multisite array, wherein the test site has the biomolecular interface layer and enzymatically oxidizing the enzyme substrate.

In another embodiment of a method for modulating the pH or ionic concentration, the method comprises:

a) providing a biosensor comprising an electromagnet in an aqueous solution and a biomolecule interface layer having one or more immobilized detection agents;

b) adding one or more enzymes immobilized onto magnetic micro- or nano-particles to the aqueous solution;

c) adding an enzyme substrate to the aqueous solution; and d) enzymatically oxidizing the enzyme substrate.

Suitable enzymes for immobilization in the biomolecular interface layer or onto the magnetic micro- or nano-particles include for example oxidases, ureases, or dehydrogenases. Such immobilized oxidase is for example a glucose oxidase and the enzyme substrate is glucose. The amounts of immobilized enzyme and enzyme substrate added can be varied in the different test sites in each of the subsets of the multisite array so as to provide a pH or ionic concentration gradient in the such subset of the multisite array.

Alternatively the enzyme is not immobilized onto a solid surface such as in the above methods being immobilized into a biomolecular interface layer or onto a magnetic micro- or nano-particle but is added to the aqueous solution in the test sites of subsets of a multisite array. Through electrolysis the enzyme undergoes a redox reaction at the electrode surface and perturbs the local pH.

In each of these embodiments the pH or ionic concentration can be further modulated by adding a buffer inhibitor to the aqueous solution. Such addition of a buffer inhibitor either assists in diffusing the produced ions of interest to the location of the biomolecular probe or detection agent or inhibits the interaction of such produced ions with buffering salts. Alternatively, in the method of modulating the pH or ionic concentration in a biosensor as described herein, the buffer inhibitor is added to the aqueous solution of the test site of subsets of a multisite array in the absence of an electrochemical active agent or immobilized enzyme. In such embodiment the buffer inhibitor is added to the aqueous solution, and facilitates the diffusion of $H^+$ ions or $OH^-$ ions that are produced at the electrodes in the test site or inhibits the interaction between $H^+$ ions or $OH^-$ ions and buffering salts.

Suitable buffer inhibitors include soluble polymers selected from poly(allylamine hydrochloride), poly(diallyldimethyl ammonium chloride), poly(vinylpyrroldone), poly(ethyleneimine), poly(vinylamine), poly(4-vinylpyridine) and tris(2-carboxyethyl)phosphine hydrochloride. The amounts of buffer inhibitor added can be varied in the different test sites in each of the subsets of the multisite array so as to provide a pH or ionic concentration gradient in the such subset of the multisite array.

The following are examples which illustrate specific methods without the intention to be limiting in any manner. The examples may be modified within the scope of the description as would be understood from the prevailing knowledge.

EXAMPLES

Electrochemical Generation of H+ or OH− Ions at Electrode Surfaces

Electrode material used: The electrode material was indium tin oxide. This is a semiconducting electrode surface with very large potential window in an aqueous solution.

Electro-Oxidation of Species to Produce H+ Ions

Figure 7A:
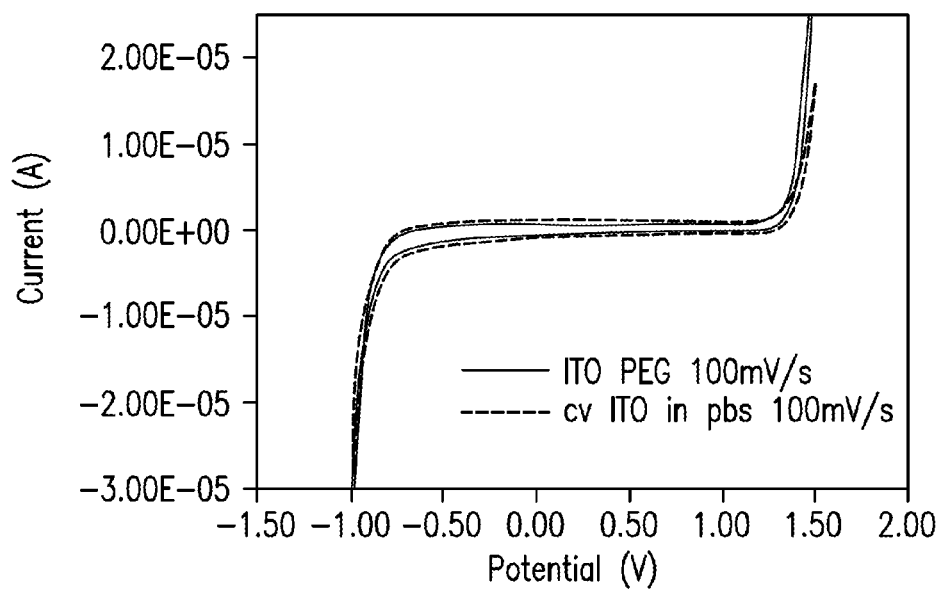
FIG. 7: A) Cyclic voltammograms of Indium Tin Oxide (ITO) electrodes in PBS only. The region where pH change can occur is where there is oxygen evolution more than 1V in respect to Ag/AgCl reference electrode. B): Cyclic voltammetric study of the oxidation of Ascorbic acid test in ITO electrodes. Current increase around 0.25V indicates the start of oxidation at ITO electrodes.
Figure 7B:
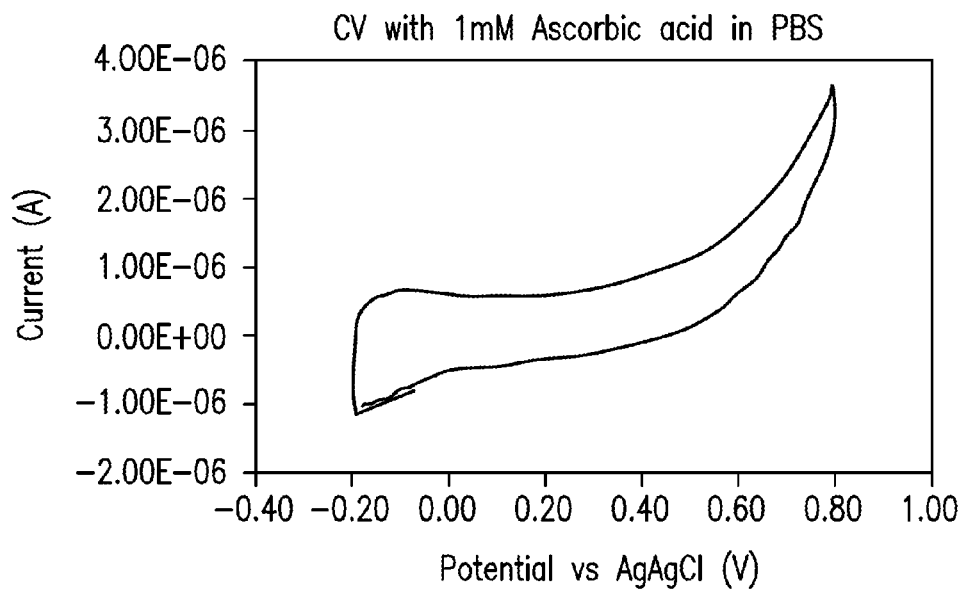
Figure 8A:
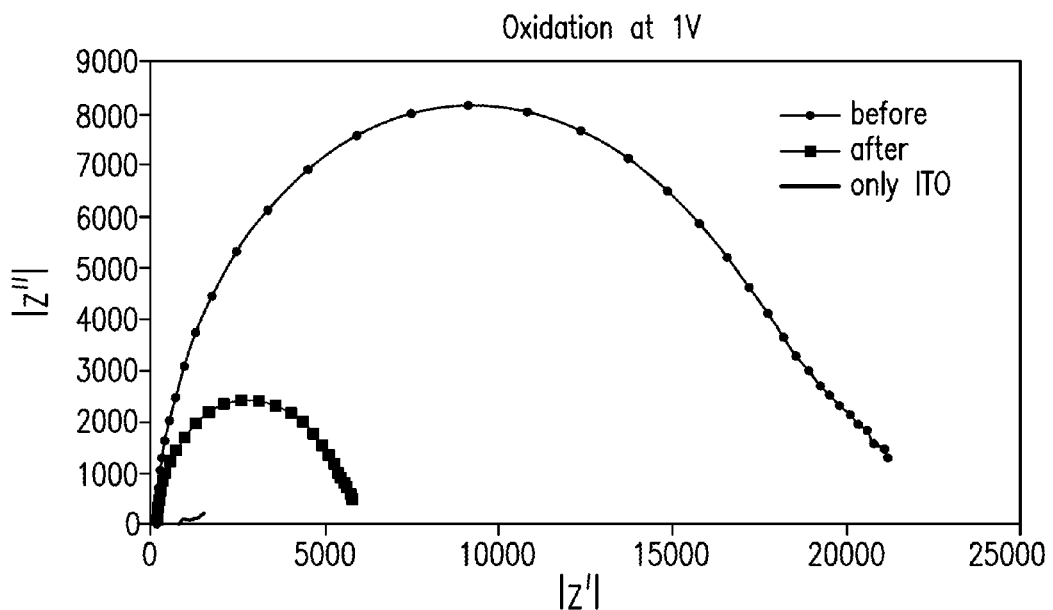
FIG. 8: A) Application of 1V on the ITO-PEG surface in Phosphate buffer. Impedance changes before and after application of 1V indicates the changes or removal of PEG from electrode. B): Oxidation of ascorbic acid at 0.5V and 0.75V at ITO-PEG surface. No change in impedance during ascorbic acid oxidation indicates PEG layers do not undergo any change.
Figure 8B:
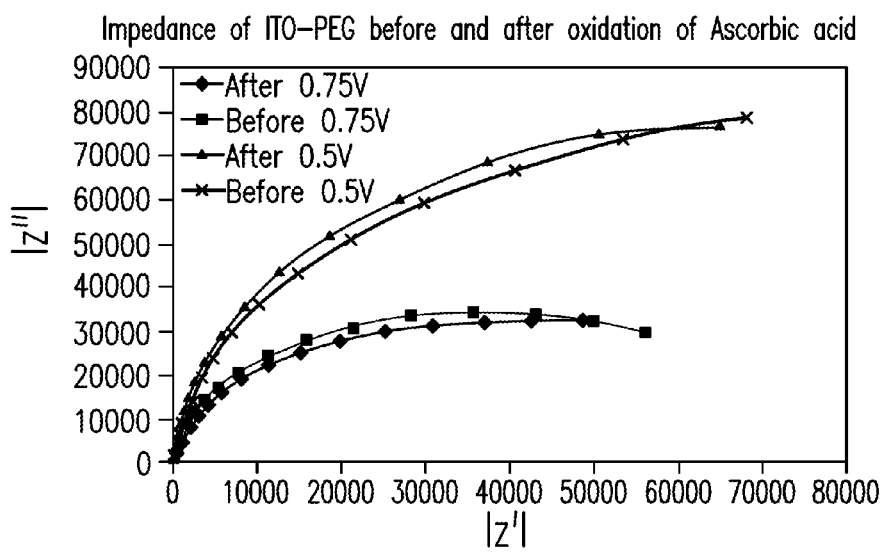

Oxidation of ascorbic acid at the electrode surfaces produced H+ ions and changed the electrode surface pH to a more acidic state:

$$AH_2 \rightarrow A + 2H^+ + 2e^-,$$

where $AH_2$ is ascorbic acid ($C_6H_6O_6$) (as shown in FIG. 5). The electrode potential at which it oxidizes was less than 0.5V for Indium tin oxide material vs Ag/AgCl reference electrode (as shown in FIG. 7). This potential was less than the voltages needed for the oxygen evolution reaction in aqueous solution. Higher electrode potential (e.g >1V for ITO electrodes in just phosphate buffer) can damage the PEG layer (as shown in FIG. 8). The ascorbic acid also acted as a sacrificial species to prevent electrochemical degradation of the surface chemistry.

Electro-Reduction of Species to Produce OH− Ions

Reduction of benzoquinone ($C_6H_4O_2$) into Hydroquinone ($C_6H_6O_2$) can produce $OH^-$ ions at −0.1V $$BQ + 2e^- + 2H_2O \rightarrow HQ + 2OH^-$$

This reduction reaction increased the pH at the electrode interface.

In the above examples the amount of $H^+$ or $OH^-$ ions generated will depend on the concentration of species present in solution (nM-mM range), potential applied (−2V to +2V), type of waveform (pulse, constant, sawtooth, sinusoidal, square wave at different frequencies and duty cycles), and diffusion of the species (can be varied due to additives in the solution). These parameters can be optimized to get different pHs at the each of the electrode element present in the multisite biosensor.

pH Change Using Enzymatic Reactions

Enzymes such as oxidases, ureases or dehydrogenases have been known to consume or generate hydrogen during the reaction. For example:

$$\beta\text{-d-glucose} + O_2 \rightarrow \text{d-glucose-}\delta\text{-lactone} + H_2O_2$$

$$\text{d-glucose-}\delta\text{-lactone} + H_2O \rightarrow \text{d-gluconate} + H^+$$

Oxidation of glucose in the presence of glucose oxidase can produce H+ ions that are used to change the pH near the proteins of interest.

Co-Immobilization of Enzymes Along with Biomolecular Probes in a Biomolecular Interface Layer The enzymes when co-immobilized on the surface along with proteins brings them in close proximity so the $H^+$ produced by the enzymatic reaction will lead to a localized pH change that can affect protein binding (for example antigen-antibody binding and non-specific binding).

Attaching the Enzymes to Magnetic Micro/Nanoparticles

Proteins are attached to micro/nanocavities of a solid surface on an electromagnet. The enzymes are separately attached to magnetic micro/nanoparticles in the solution. Controlling the electromagnet that is fabricated/placed underneath controls the local pH values. Then the enzymatic reaction is triggered by introducing the corresponding enzyme substrate (as shown in FIG. 6). Alternatively electrochemically active enzymes are used. The pH change is localized on the cavities and the protein interactions are modulated.

What is claimed is:

1. A method comprising:
    a) providing a biosensor comprising a multisite array of test sites, each test site comprising a support in an aqueous solution, the support comprising one or more electrodes or an electromagnet, and a biomolecule interface layer having one or more immobilized probes thereon;
    b) adding an electrochemically active agent, an enzyme, an enzyme substrate, a buffer inhibitor, or a combination thereof to the aqueous solution;
    c) during a test, independently varying for each of the test sites a degree of biological interaction that can occur with a biomolecule analyte at the respective test site, to obtain a collection of varied signals, wherein the varying includes reacting the electrochemically active agent, the enzyme, the enzyme substrate, or combination thereof in the aqueous solution to produce $H^+$ ion or $OH^-$ ions, or increasing the diffusion of $H^+$ ions or $OH^-$ ions with the buffer inhibitor, or inhibiting the interaction between $H^+$ ions or $OH^-$ ions and buffering salts with the buffer inhibitor; and
    d) analyzing the collection of varied signals to obtain a measurement.

2. A method of modulating the pH or ionic concentration in a biosensor, the method comprising:
    a) providing a biosensor comprising a multisite array of test sites in which the conditions for interacting with a biomolecule analyte can be varied independently, each test site comprising a support in an aqueous solution, the support comprising one or more electrodes or an electromagnet, and a biomolecule interface layer having one or more immobilized probes thereon;
    b) adding an electrochemically active agent, an enzyme, an enzyme substrate, a buffer inhibitor, or a combination thereof to the aqueous solution; and
    c) reacting the electrochemically active agent, the enzyme, the enzyme substrate, or combination thereof in the aqueous solution to produce $H^+$ ion or $OH^-$ ions, or increasing the diffusion of $H^+$ ions or $OH^-$ ions with the buffer inhibitor, or inhibiting the interaction between $H^+$ ions or $OH^-$ ions and buffering salts with the buffer inhibitor;
    wherein:
        the aqueous solution comprises a water-miscible organic co-solvent selected from the groups consisting of acetonitrile, dimethyl sulfoxide (DMSO), dimethyl formamide (DMF), N,N-dimethyl acetamide (DMAc), and mixtures thereof;
        the biomolecular interface layer comprises a silane immobilized polyethylene glycol (PEG), and at least a portion of the surface-immobilized PEG comprises terminal functional groups selected from the group consisting N-hydroxysuccinimide (NHS) ester, maleimide, alkynes, azides, streptavidin and biotin;
        the biosensor comprises a support in an aqueous solution, the support comprising one or more electrodes, and a biomolecule interface layer having one or more immobilized probes and one or more immobilized enzymes, in step b) an enzyme substrate is added to the aqueous solution, and in step c) the enzyme substrate is enzymatically oxidized or reduced; or
        the support comprises an electromagnet and the biomolecule interface layer has one or more immobilized probes, in step b) one or more enzymes immobilized onto magnetic micro- or nano-particles are added prior to or simultaneously with an enzyme substrate, and in step c) the enzyme substrate is enzymatically oxidized or reduced.

3. The method of modulating the pH or ionic concentration in a biosensor according to claim 1, wherein the biomolecular interface layer having one or more immobilized probes thereon comprises a layer of immobilized polymers and the probes.

4. The method of modulating the pH or ionic concentration in a biosensor according to claim 2, wherein the biomolecular interface layer comprises the silane immobilized polyethylene glycol (PEG), and at least a portion of the surface-immobilized PEG comprises the terminal functional groups selected from the group consisting N-hydroxysuccinimide (NHS) ester, maleimide, alkynes, azides, streptavidin and biotin.

5. The method of modulating the pH or ionic concentration in a biosensor according to claim 1, wherein in step b) an electrochemically active agent is added to the aqueous solution, and in step c) the electrochemically active agent is oxidized or reduced.

6. The method of modulating the pH or ionic concentration in a biosensor according to claim 5, wherein the electrode potential is in the range of −1V to +1V vs Ag/AgCl.

7. The method of modulating the pH or ionic concentration in a biosensor according to claim 5, further comprising adding a buffer inhibitor to the aqueous solution.

8. The method of modulating the pH or ionic concentration in a biosensor according to claim 1, wherein the electrochemically active agent is added at a concentration of 1 nM to 100 mM.

9. The method of modulating the pH or ionic concentration in a biosensor according to claim 1, wherein the electrochemically active agent is selected from the group consisting of dopamine hydrochloride, ascorbic acid, phenol and derivatives thereof, benzoquinones and derivatives thereof, naphthoquinones and derivatives thereof, and 9,10-anthraquinone and derivatives thereof.

10. The method of modulating the pH or ionic concentration in a biosensor according to claim 1, wherein the buffer inhibitor is a soluble polymer selected from poly(allylamine hydrochloride), poly(diallyldimethyl ammonium chloride), poly(vinylpyrroldone), poly(ethyleneimine), poly(vinylamine), poly(4-vinylpyridine) and tris(2-carboxyethyl) phosphine hydrochloride.

11. The method of modulating the pH or ionic concentration in a biosensor according to claim 1, wherein the biosensor comprises a CMOS, electrode array, or TFT based system.

12. The method of modulating the pH or ionic concentration in a biosensor according to claim 1, wherein the electrode is an indium tin oxide, gold or silver electrode.

13. The method of modulating the pH or ionic concentration in a biosensor according to claim 12, wherein the protein is an antibody.

14. The method of modulating the pH or ionic concentration in a biosensor according to claim 1, wherein the support is a glass or plastic support.

15. The method of modulating the pH or ionic concentration in a biosensor according to claim 1, wherein the immobilized probe is selected from a protein, a peptide, a nucleic acid and a cell.

16. The method of modulating the pH or ionic concentration in a biosensor according to claim 2, wherein the aqueous solution comprises the water-miscible organic co-solvent selected from the groups consisting of acetonitrile, dimethyl sulfoxide (DMSO), dimethyl formamide (DMF), N,N-dimethyl acetamide (DMAc), and mixtures thereof.

17. The method of modulating the pH or ionic concentration in a biosensor according to claim 2, wherein the biosensor comprises the support in the aqueous solution, the support comprising the one or more electrodes, and the biomolecule interface layer having the one or more immobilized probes and one or more immobilized enzymes, in step b) the enzyme substrate is added to the aqueous solution, and in step c) the enzyme substrate is enzymatically oxidized or reduced.

18. The method of modulating the pH or ionic concentration in a biosensor according to claim 17, wherein the immobilized enzyme is an oxidase, urease, or dehydrogenase.

19. The method of modulating the pH or ionic concentration in a biosensor according to claim 17, further comprising adding a buffer inhibitor to the aqueous solution.

20. The method of modulating the pH or ionic concentration in a biosensor according to claim 2, wherein the support comprises the electromagnet and the biomolecule interface layer has the one or more immobilized probes, in step b) the one or more enzymes immobilized onto magnetic micro- or nano-particles are added prior to or simultaneously with the enzyme substrate, and in step c) the enzyme substrate is enzymatically oxidized or reduced.

21. The method of modulating the pH or ionic concentration in a biosensor according to claim 20, wherein the immobilized enzyme is an oxidase, urease, or dehydrogenase.

22. The method of modulating the pH or ionic concentration in a biosensor according to claim 20, further comprising adding a buffer inhibitor to the aqueous solution.

23. A method of modulating the pH or ionic concentration in a biosensor, the method comprising:
   a) providing a biosensor comprising a multisite array of test sites in which the conditions for interacting with a biomolecule analyte can be varied independently, each test site comprising a support in an aqueous solution, the support comprising one or more electrodes or an electromagnet, and a biomolecule interface layer having one or more immobilized probes thereon;
   b) adding an enzyme to the aqueous solution; and
   c) reacting the enzyme at the electrode surface.

24. The method of modulating the pH or ionic concentration in a biosensor according to claim 23, further comprising adding a buffer inhibitor to the aqueous solution.

25. A method of modulating the pH or ionic concentration in a biosensor, the method comprising:
   a) providing a biosensor comprising a multisite array of test sites in which the conditions for interacting with a biomolecule analyte can be varied independently, each test site comprising a support in an aqueous solution, the support comprising one or more electrodes or an electromagnet, and a biomolecule interface layer having one or more immobilized probes thereon;
   b) adding a buffer inhibitor to the aqueous solution; and
   c) reacting the electrochemically active agent, the enzyme, the enzyme substrate, or combination thereof in the aqueous solution to produce $H^+$ ion or $OH^-$ ions, or increasing diffusion of $H^+$ ions or $OH^-$ ions with the buffer inhibitor, or inhibiting the interaction between $H^+$ ions or $OH^-$ ions and buffering salts is inhibited with the buffer inhibitor.

26. A method of modulating the pH or ionic concentration in a biosensor, the method comprising:
   a) providing a biosensor comprising a multisite array of test sites in which the conditions for interacting with a biomolecule analyte can be varied independently, each test site comprising a support in an aqueous solution, the support comprising one or more electrodes or an electromagnet, and a biomolecule interface layer having one or more immobilized probes thereon, wherein the biomolecule interface layer is covering the one or more electrodes and has a thickness of 5-150 nm;
   b) adding an electrochemically active agent, an enzyme, an enzyme substrate, a buffer inhibitor, or a combination thereof to the aqueous solution; and
   c) reacting the electrochemically active agent, the enzyme, the enzyme substrate, or combination thereof in the aqueous solution to produce $H^+$ ion or $OH-$ ions, or increasing the diffusion of $H^+$ ions or $OH^-$ ions with the buffer inhibitor, or inhibiting the interaction between $H^+$ ions or $OH^-$ ions and buffering salts with the buffer inhibitor.

27. A biosensor for use in detecting a biomolecule analyte comprising:
   a multisite array of test sites, each test site comprising: a support in an aqueous solution: wherein
      the aqueous solution has added thereto an electrochemically active agent, an enzyme, an enzyme substrate, a buffer inhibitor, or a combination thereof;
      the support comprises one or more electrodes or an electromagnet, and a biomolecule interface layer having one or more immobilized probes thereon; and
      the biosensor is configured for:
         during a test, independently varying for each of the test sites a degree of biological interaction that can occur with a biomolecule analyte at the respective test site, to obtain a collection of varied signals, the varying including reacting the electrochemically active agent, the enzyme, the enzyme substrate, or combination thereof in the aqueous solution to produce $H^+$ ion or $OH^-$ ions, or increasing the diffusion of $H^+$ ions or $OH^-$ ions with the buffer inhibitor, or inhibiting the interaction between $H^+$ ions or $OH^-$ ions and buffering salts with the buffer inhibitor; and
         analyzing the collection of varied signals to obtain a measurement.

28. The biosensor according to claim 27, wherein the support comprises the electromagnet.

29. The biosensor according to claim 27, wherein the biosensor comprises a CMOS, electrode array, or TFT based system.

30. The biosensor according to claim 27, wherein the electrode is an indium tin oxide, gold or silver electrode.

31. The biosensor according to claim 27, wherein the support is a glass or plastic support.

32. The biosensor according to claim 27, wherein the immobilized probe is selected from a protein, a peptide, a nucleic acid and a cell.

33. A method for detecting a biomolecule analyte in a biological sample, the method comprising:
a) providing a biosensor comprising a multisite array of test sites in which the conditions for interacting with a biomolecule analyte can be varied independently, each test site comprising a support in an aqueous solution, the support comprising one or more electrodes or an electromagnet, and a biomolecule interface layer having one or more immobilized probes thereon;
b) adding in each test site an electrochemically active agent, an enzyme, an enzyme substrate, a buffer inhibitor, or a combination thereof to the aqueous solution;
c) reacting the electrochemically active agent, the enzyme, the enzyme substrate, or a combination thereof in the aqueous solution to produce $H^+$ ion or $OH^-$ ions, or increasing the diffusion of $H^+$ ions or $OH^-$ ions with a buffer inhibitor, or inhibiting the interaction between $H^+$ ions or $OH^-$ ions and buffering salts with the buffer inhibitor;
d) adding a biological sample to each test site; and
e) detecting the biomolecule analyte in each test site,
wherein the amounts added in step b) and the reaction in step c) are varied between test sites in a subset array of test sites in order to obtain sets of test sites in which the pH or ionic concentration near electrode surfaces in the test sites varies.

34. The method for detecting a biomolecule analyte in a biological sample according to claim 33, wherein amount of biological sample or the concentration of the biological sample is varied between subset arrays of test sites.

35. The method for detecting a biomolecule analyte in a biological sample according to claim 33, wherein the aqueous solution comprises a water-miscible organic co-solvent selected from the groups consisting of acetonitrile, dimethyl sulfoxide (DMSO), dimethyl formamide (DMF), N,N-dimethyl acetamide (DMAc), and mixtures thereof.

* * * * *